(12) United States Patent
Stetzel

(10) Patent No.: US 6,692,692 B2
(45) Date of Patent: Feb. 17, 2004

(54) DENTAL DRILL STERILIZATION THROUGH APPLICATION OF HIGH AMPERAGE CURRENT

(76) Inventor: Eric J. Stetzel, 2810 Meadow Stream, Ft. Wayne, IN (US) 46825

( * ) Notice: Subject to any disclaimer, the term of this patent is extended or adjusted under 35 U.S.C. 154(b) by 35 days.

(21) Appl. No.: 10/134,767

(22) Filed: Apr. 29, 2002

(65) Prior Publication Data

US 2003/0202901 A1 Oct. 30, 2003

(51) Int. Cl.[7] .................................................. A61L 9/00
(52) U.S. Cl. ........................ 422/3; 219/233; 219/229; 219/533; 422/1; 422/22; 422/307; 433/80; 433/104
(58) Field of Search .......................... 422/1, 3, 22, 307; 219/233, 229, 533; 433/80, 104

(56) References Cited

U.S. PATENT DOCUMENTS

| | | |
|---|---|---|
| 4,242,462 A | 12/1980 | Thomas |
| 5,204,632 A | 4/1993 | Leach |
| 5,333,146 A | 7/1994 | Vance |
| 5,336,862 A | 8/1994 | Yelvington |
| 5,407,354 A | 4/1995 | Fife |
| 5,468,928 A | 11/1995 | Yelvington |
| 5,480,302 A | 1/1996 | Fife |
| 5,520,893 A | 5/1996 | Kasting, Jr. et al. |
| 5,648,003 A | * 7/1997 | Liang et al. ................. 219/211 |
| 6,146,586 A | * 11/2000 | McLeod et al. ............... 422/23 |

* cited by examiner

*Primary Examiner*—Krisanne Thornton
(74) *Attorney, Agent, or Firm*—Baker & Daniels

(57) ABSTRACT

The present invention involves a sterilization system for running high amperage current through a dental or medical handpiece to be sterilized thereby heating the handpiece to a point of sterilization. The system includes a controller, a high amperage current source, and a handpiece receptacle. The handpiece receptacle includes clamps to hold the handpiece in place and a temperature sensor to measure the temperature of the handpiece. The controller controls the amount of current supplied by the high amperage current source to the handpiece according to the temperature of the handpiece. After the handpiece has been at or above the sterilization temperature for the required period of time, the controller stops the flow of current to the handpiece.

20 Claims, 5 Drawing Sheets

DENTAL DRILL STERILIZATION THROUGH APPLICATION OF HIGH AMPERAGE CURRENT

BACKGROUND OF THE INVENTION

1. Field of the Invention

The present invention generally relates to systems for sterilization, and more particularly to systems for sterilizing dental drills or other medical instruments.

2. Description of the Related Art

Prevention of contamination and cross-contamination have long been matters of primary concern in the dental/medical field. Where handpiece instruments must be reused on successive patients care is required as are certain antimicrobial steps to prevent transmission of virally or bacterially caused infections from one patient to another. Another concern is to obviate transmission of such infections from or to the health care provider.

An increasing awareness of the potential for the spread of highly contagious viral and bacterial diseases has led to further emphasis being placed on infection control in the dental operatory. The American Dental Association (ADA) and the Centers for Disease Control (CDC) have been instrumental in publishing guidelines intended to reduce the opportunity for disease transmission during the practice of dentistry. These recommendations support the use of protective apparel by dental professionals whose ordinary duties require hands-on contact with patient body fluids, instrumentation and materials used in dental procedures. It is also recommended that non-disposable instrumentation and materials used in the dental operatory be at least disinfected.

"Sterilization" is the process by which micro-organisms are destroyed, including viruses, bacteria, fungi, and spores. Sterilization may be achieved by (1) steam under pressure (autoclave), (2) prolonged dry heat, (3) chemical vapor, (4) ethylene oxide gas, and (5) submersion on in chemical sterilants. "Disinfection" is less lethal to microbials than sterilization and typically requires application of a chemical registered with the Environmental Protection Agency (EPA).

The ADA has recommended that high-quality disposable medical gloves, a surgical mask covering the nose and mouth, and protective eye wear be worn by dental professionals due to constant exposure to patient-contaminated coolant aerosols associated with high speed handpieces as well as exudates of blood, pus, saliva, oral tissue, and decayed tooth material. It is recommended that the dental assistant and the hygienist wear disposable medical gloves. Hand washing and use of oral rinses, a rubber dam, and a saliva evacuation system are also encouraged. Training each health care provider is also important.

The ADA has also recommended autoclaving for instruments and non-disposable materials that are able to withstand the high heat of an autoclave cycle. Non-autoclavable instrumentation and materials should be chemically disinfected with a properly diluted, and freshly prepared disinfectant solution according to the manufacturer's instructions. Large equipment in the dentists' office should be "wiped down" routinely with a suitable anti-microbial solution. Significantly, hepatitis B and HIV are heat sensitive viruses, which are essentially rendered non-contagious by short-term autoclaving.

Except for a suggestion of wiping the handpiece routinely with recommended "wipe down" disinfectants, there is, to our knowledge, no other ADA recommended technique for the disinfection of heat intolerant handpieces between patients. And yet, the handpiece is subjected to the exact same patient-contaminated coolant aerosols and exudates as are the dentist's hands, nose and mouth, and eyes. The handpiece is not only subjected to the contaminated material cast onto it by the coolant aerosol and the mechanical rotation of the tool, but also contaminants transferred to the handpiece by the dentist's glove. Thus, a potential source of cross-contamination from patient to patient exists through the handpieces and microbial contaminants surviving the disinfectant wipe are likely to be transferred to subsequent patients on the newly-donned gloves of the dental professional. Handpieces in today's technology have turbine blades which spin at more or less 500,000 revolutions per minute under air pressure. When the air and/or water pressures are turned off, a vacuum is created which may suck blood, saliva, and serum into the handpiece as a potential source for cross-contamination.

Transmission of microbials through the air in dental offices is also a matter of substantial concern.

Diseases of concern comprise the common cold, hepatitis B (HBV), non-A/non-B hepatitis, influenza, measles (German and rubeola), tuberculosis, staphylococcus, and streptococcus, herpes infections including chicken pox, infectious mononucleosis, epstein bar, herpetic whitlow, herpetic conjunctivitis, and AIDS (the HIV [human immunodeficiency virus] virus).

While it is clear that autoclave sterilization is the antimicrobial treatment of choice, the cost of buying, operating, and maintaining autoclave equipment is high and more handpieces need to be purchased and utilized where handpiece autoclaving occurs between each patient. Also, as stated above, not all handpieces can withstand the heat of autoclaving.

Thus, many doctors today, however, appear to find it impractical to sterilize handpieces after each patient use because of possible damage to the devices and the necessary burdensome financial investment in multiple handpieces required to maintain an acceptable instrument flow. Nevertheless, the CDC currently recommends heat treatment of all handpieces using also acceptable methods which assure internal and external sterility between patients.

SUMMARY OF THE INVENTION

The present invention involves a sterilization system running high amperage current through a dental handpiece to be sterilized thereby heating the dental handpiece to a point of sterilization. The system includes a controller, a high amperage current source, and a dental handpiece receptacle. The dental handpiece receptacle includes clamps to hold the handpiece in place and a temperature sensor to measure the temperature of the dental handpiece. The controller controls the amount of current supplied by the high amperage current source to the dental handpiece according to the temperature of the dental handpiece. After the dental handpiece has been at or above the sterilization temperature for the required period of time, the controller stops the flow of current to the dental handpiece.

The present invention provides a sterilization system for a dental or medical handpiece comprising a variable high amperage current source providing an output current, a handpiece receptacle having clamps for attaching the handpiece, and a controller. The clamps are electrically connected to the high amperage current source. The controller is electrically connected to the high amperage current source to control the output current of the high amperage current source to the handpiece.

The present invention also provides a system sterilization system for a dental or medical handpiece comprising a variable high amperage current source providing an output current, a handpiece receptacle having clamps for attaching the handpiece, a temperature sensor, and a controller. The clamps are electrically connected to the high amperage current source. The temperature sensor measures the temperature of the handpiece. The controller has a microprocessor and is electrically connected to the temperature sensor and the high amperage current source to control the output current of the high amperage current source to the handpiece depending on the temperature of the handpiece.

The present invention further provides a sterilization system for a dental or medical handpiece comprising clamps for holding the handpiece, current means for supplying high amperage current through the clamps to the handpiece, and control means for adjusting the current means.

The present invention still further provides a method of sterilizing a dental or medical handpiece having a handpiece receptacle with clamps and a high amperage current source. The steps comprise placing the handpiece in the clamps of the handpiece receptacle, providing current through the handpiece with the high amperage current source, measuring the temperature of the handpiece, comparing the temperature of the handpiece with predetermined low and high temperature limits, adjusting the current provided by the high amperage current source to keep the measured temperature between the predetermined low and high temperature limits, measuring the amount of time the measure temperature has been within the low and high temperature limits, and stopping the current through the handpiece when the measured time has reached a predetermined limit.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
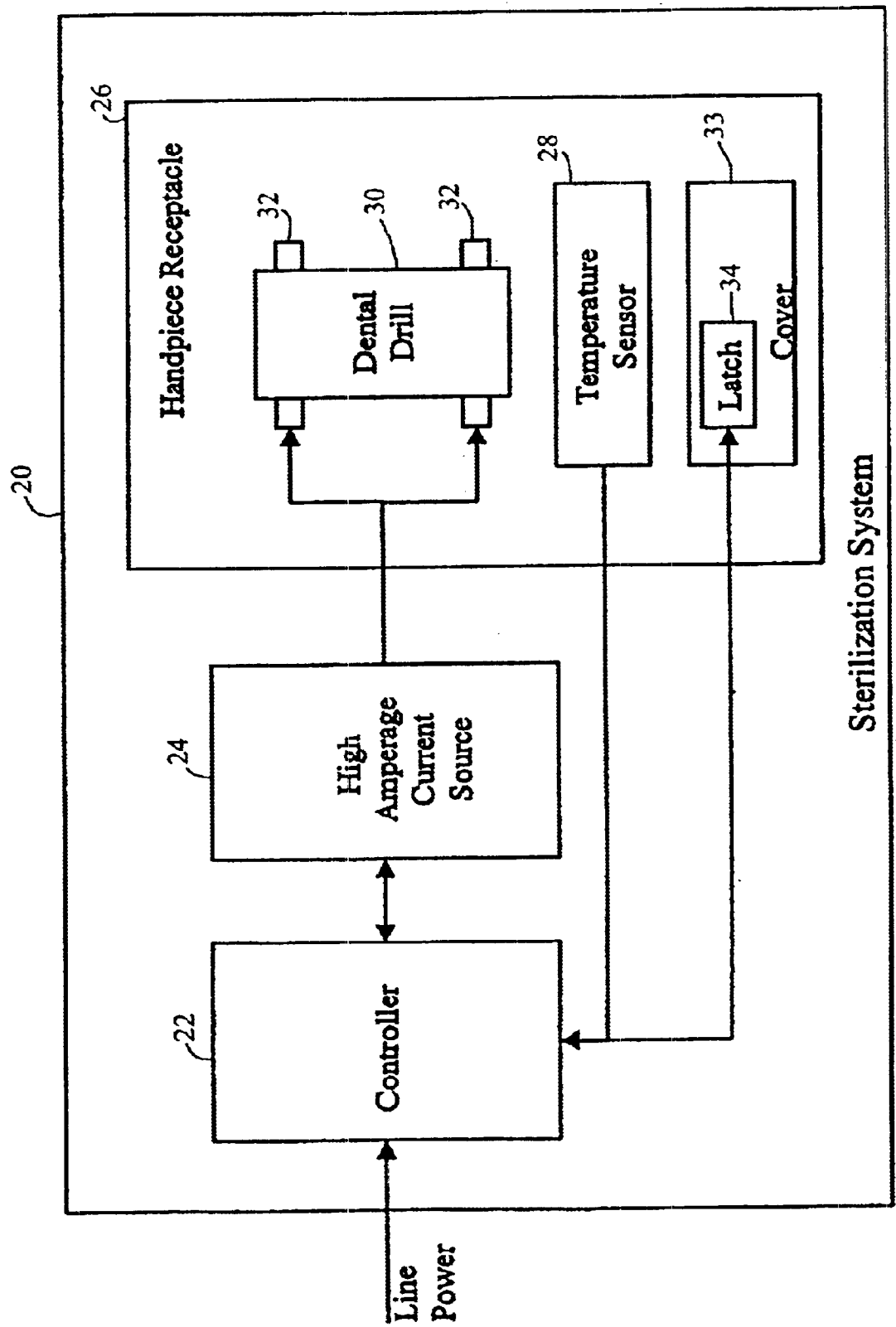
FIG. 1 is a block diagram of a dental sterilization system according to the present invention.

Corresponding reference characters indicate corresponding parts throughout the several views. Although the drawings represent an embodiment of the present invention, the drawings are not necessarily to scale and certain features may be exaggerated in order to better illustrate and explain the present invention. The exemplification set out herein illustrates an embodiment of the invention, in one form, and such exemplification is not to be construed as limiting the scope of the invention in any manner.

DESCRIPTION OF THE PRESENT INVENTION

The embodiment disclosed below is not intended to be exhaustive or limit the invention to the precise form disclosed in the following detailed description. Rather, the embodiment is chosen and described so that others skilled in the art may utilize its teachings.

Referring to FIG. 1, a sterilization system, in accordance with the present invention and generally referenced as 20, includes controller 22, high amperage current source 24, and handpiece receptacle 26. Controller 22 controls high amperage current source 24 which provides an output of high amperage current through handpiece 30, such as a dental drill or other medical instrument, held in dental handpiece receptacle 26. Handpiece receptacle includes temperature sensor 28, clamps 32 for holding handpiece 30 and providing electrical connections for the high amperage current, and cover 33 with latch 34 which when activated prevents access to or removal of handpiece 30 when either current is flowing through handpiece 30 or the temperature of handpiece 30 is above a predetermined safe handling temperature. Clamps 32 are connected to high amperage current source 24 via high amperage current wire. Controller 22 maintains the temperature of handpiece 30 within a predetermined temperature range for a specified period of time to insure proper sterilization of handpiece 30. The predetermined temperature range ensures the temperature is adequate for sterilization and includes a low temperature limit and a high temperature limit.

Figure 2:
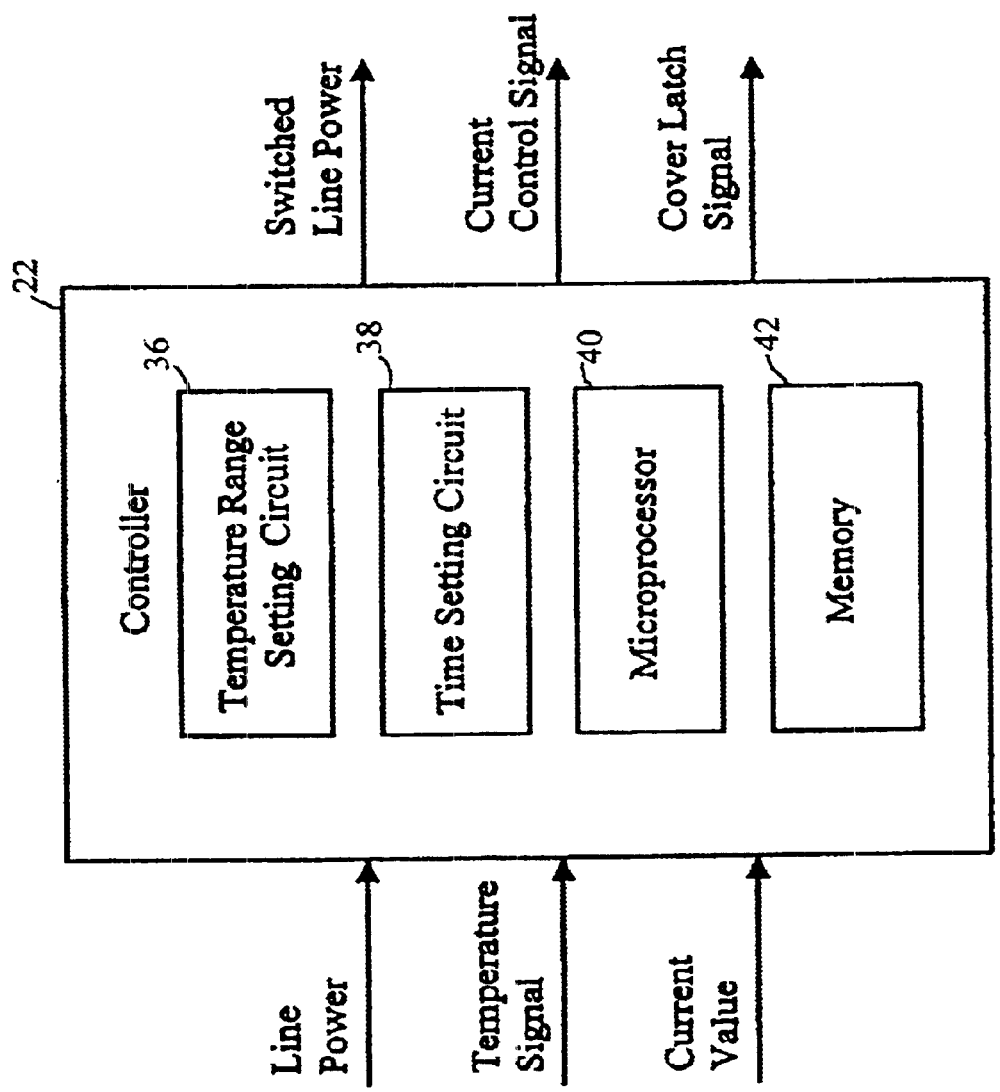
FIG. 2 is a block diagram of the controller of the system of FIG. 1.

Controller 22 in FIG. 2 receives line power from a standard 110 volt A.C. external power source (not shown) to operate and includes temperature range setting circuit 36, time setting circuit 38, microprocessor 40, and memory 42. Microprocessor 40 receives a temperature signal representing the temperature of handpiece 30 from temperature sensor 28 in handpiece receptacle 26 and a current value representing the amount of current being supplied by high amperage current source 24. Depending on the value of the temperature signal and the amount of time spent above a specific temperature, controller 22 may increase, decrease, or stop the flow of high amperage current to handpiece 30 through clamps 32.

Controller 22 also controls the function of latch 34 of handpiece receptacle 26. If high amperage current source 24 is providing current to handpiece 30 or the temperature of handpiece 30 is greater than a predetermined safe handling temperature, controller 22 will command latch 34 to lock cover 33 shut preventing access to handpiece 30. Otherwise controller 22 commands latch 34 to unlock cover 33 allowing access to install or remove handpiece 30.

Temperature range setting circuit 36 allows the operator of sterilization system 20 to choose the temperature range (e.g., low and high limits) that the temperature of handpiece 30 will be maintained by controller 22 to achieve sterilization of handpiece 30. Temperature range setting circuit 36 may include a pair of potentiometers, a pair of thumbwheel switches, a digital keypad, or other settable devices coupled to microcontroller 40 in controller 22 to serve as indicators of the temperature range.

Time setting circuit 38 allows the operator of sterilization system 20 to choose a time limit that corresponds to the amount of time that the temperature of handpiece 30 must be at or above the temperature range to achieve sterilization of handpiece 30. Likewise, time setting circuit 38 may include a potentiometer, a thumbwheel switch, a digital keypad, or other settable device coupled to microprocessor 40 in controller 22 to serve as indicator of the sterilization time.

Memory 42 contains the software routines run by microprocessor 40, constant values describing some of the set variables of sterilization system 20, a predetermined value for the safe handling temperature, and predetermined values for the temperature range and the time limit, any of which may serve as indicators of the temperature range or sterilization time if temperature range setting circuit 36 and time setting circuit 38 do not include a physical setting device sterilization system 20.

High amperage current source 24 is controlled by controller 22 and provides a variable D.C. current very similar to that of a welder to handpiece 30. High amperage current source 24 receives the line power which may be switched on or off by controller 22 and a current control signal to regulate the D.C. current output. The switched A.C. line power is introduced to a transformer in high amperage current source 24 which converts the electrical energy from the external power source to D.C. current at 24 volts with a current maximum of 300 amps which will be introduced into handpiece 30. The current control signal can increase or decrease the amount of current sent through handpiece 30 to regulate the temperature of handpiece 30.

Figure 3A:
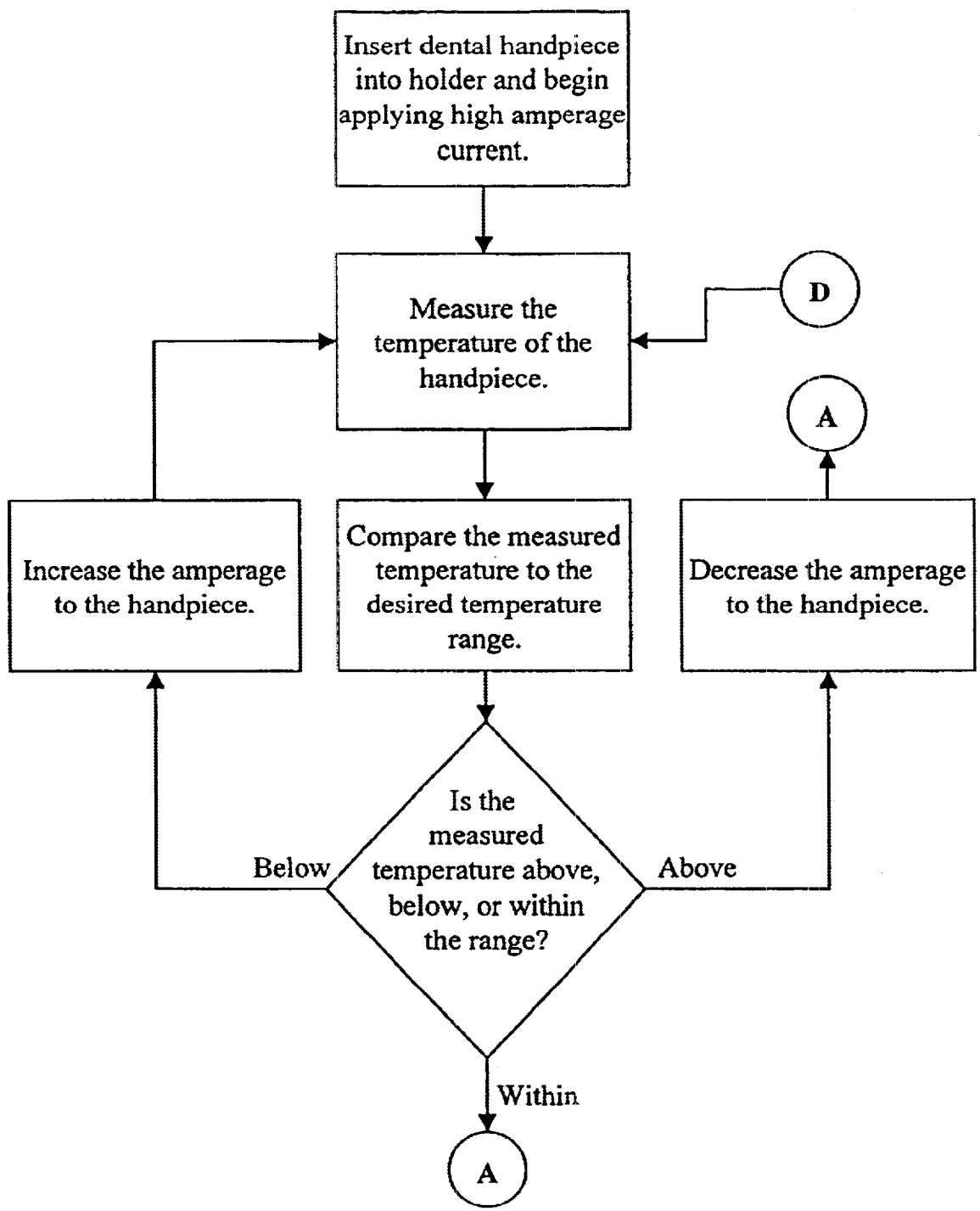
FIGS. 3A through 3C are a flow diagram of a method of sterilizing a dental handpiece using the system in FIG. 1.
Figure 3B:
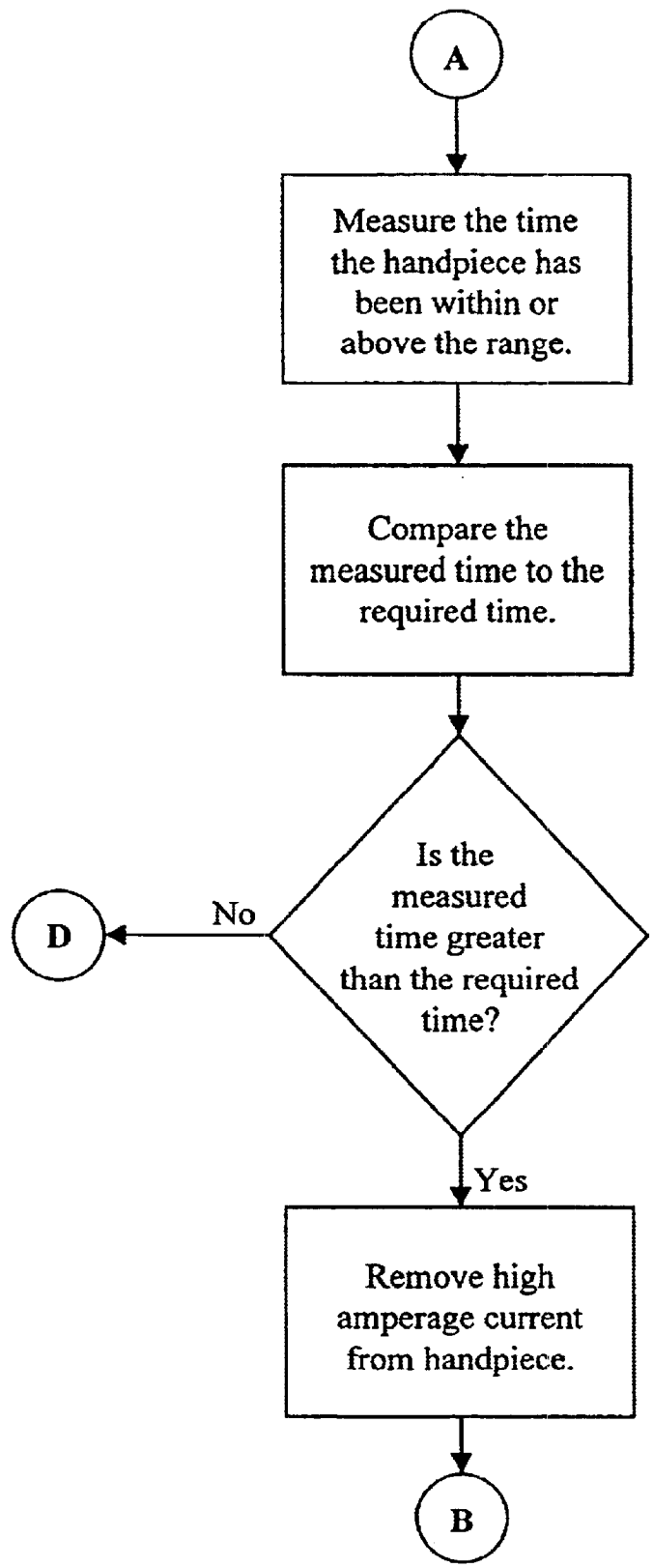
Figure 3C:
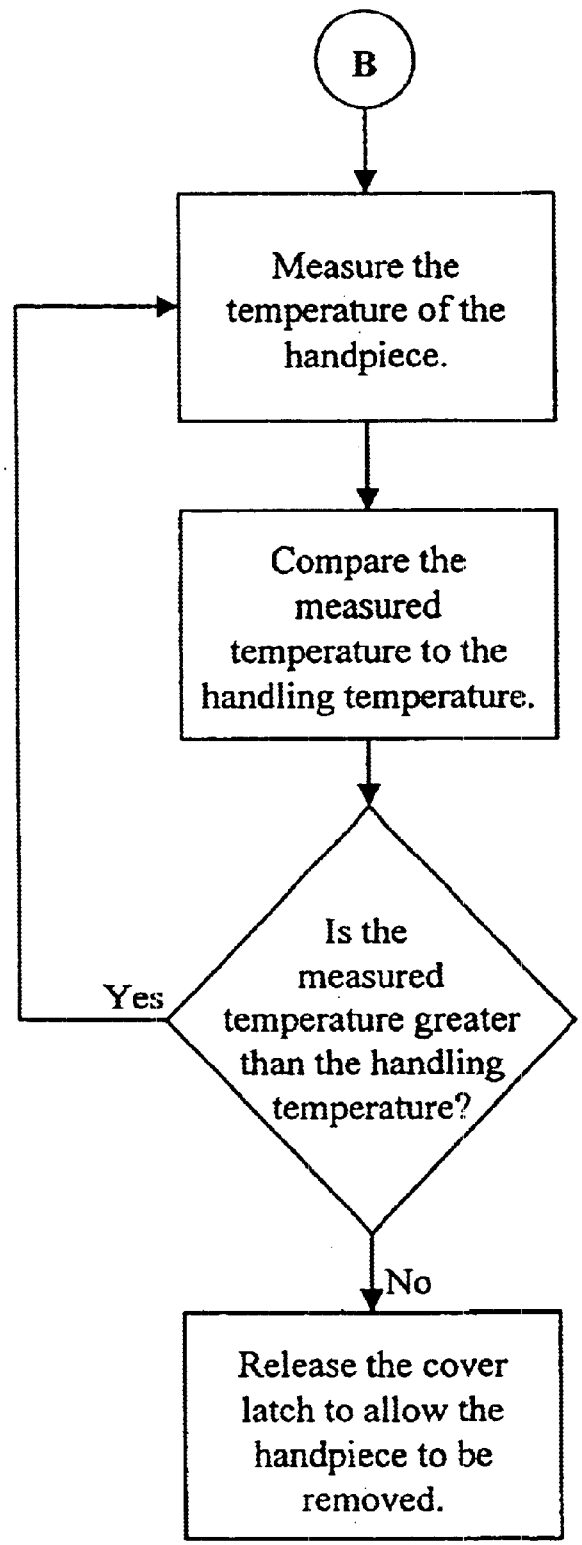

FIGS. 3A to 3C show in flow draft form a method for sterilizing a dental handpiece using the above described embodiment. A dental handpiece is inserted into a handpiece receptacle and high amperage current is applied to the dental handpiece through the receptacle. The temperature of the handpiece is measured and compared to the desired sterilization temperature range. The desired temperature range may be a predetermined range stored in the memory or a range selected by the operator. If the measured temperature is below the desired temperature range, the current to the handpiece will be increased and the temperature of the handpiece is measured again and compared to the temperature range to continue the process. If the measured temperature is above the temperature range, the current to the handpiece is decreased.

If the measured temperature is above or within the desired temperature range, the system measures the time the handpiece has been above or within the temperature range and compares the measured time to the required sterilization time. The required sterilization time may likewise be a predetermined valued stored in the memory or a value selected by the operator. If the measured time is less than the required time, then the temperature of the dental handpiece is measured again and compared to the temperature range to continue the process. If the measured time is greater than the required time, then the current is removed from the handpiece.

Then the temperature of the dental handpiece is measured and compared to a predetermined safe handling temperature. If the measured temperature is greater than the safe handling temperature, then the temperature of the dental handpiece is measured again and compared to the safe handling temperature to continue the process. If the measured temperature is less than the safe handling temperature, then the cover latch is released and the dental handpiece can be removed from the receptacle. As with the temperature range and sterilization time, the safe handling temperature may be indicated by an external input, a stored value, or a programmable stored value.

While the present invention has been described as sterilizing a medical or dental handpiece, it is envisioned that other similar medical devices or other items requiring sterilization could be sterilized using the above described embodiment and method. Furthermore, it is envisioned that the system could sterilize multiple devices by adding additional clamps and circuitry.

The advantages of using this type system for sterilization is that the cost of the present invention would be significantly less than the cost of an autoclave and does not require the use of a chemical registered with the EPA.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A sterilization system for a handpiece of a medical or dental device, the sterilization system comprising:

current source capable of providing a variable high amperage output current;

a handpiece receptacle having clamps for attaching the handpiece, said clamps electrically connected to said current source; and a controller electrically connected to said current source to control said output current of said current source to the handpiece, said controller including programming to apply said output current at a sufficient amperage for a sufficient time to heat the handpiece to be sterilized.

2. The system of claim 1 further comprising a temperature sensor coupled to said handpiece receptacle and located proximate the handpiece to provide a handpiece temperature signal to said controller.

3. The system of claim 2, wherein said controller includes a microprocessor and memory.

4. The system of claim 3 further comprising a low temperature limit and high temperature limit indicator, said microprocessor adjusting said output current of said current source to the handpiece to keep said handpiece temperature signal between said low temperature limit and said high temperature limit.

5. The system of claim 4 further comprising a sterilization time indicator, said microprocessor removing said output current of said current source from the handpiece after said handpiece temperature signal has been above said low temperature for said sterilization time.

6. The system of claim 3 further comprising a safe handling temperature limit indicator, said microprocessor causing said handpiece receptacle to deny access to the handpiece until said handpiece temperature signal is less than said handling temperature limit.

7. The system of claim 1 further comprising temperature range setting means for allowing the manual setting of a low sterilization temperature limit and a high sterilization temperature limit, said temperature range setting means coupled to said controller.

8. The system of claim 1 further comprising time setting means for allowing the manual setting of a sterilization time, said time setting means coupled to said controller.

9. The system of claim 1, wherein said handpiece receptacle includes a cover having a cover latch, said controller being electrically coupled to said cover latch and adapted to command locking or unlocking of said cover latch thereby restricting access to the handpiece during the sterilization process.

10. A sterilization system for a handpiece of a medical or dental device, the sterilization system comprising:

current source capable of providing a variable high amperage output current;

a handpiece receptacle having clamps for attaching the handpiece in a set position, said clamps electrically connected to said current source;

a temperature sensor associated with said handpiece receptacle and located proximate said set position; and a controller having a microprocessor and electrically connected to said temperature sensor and said current source to control said output current of said current source to the handpiece depending on the measured temperature of the handpiece.

11. The system of claim 10 further comprising temperature range setting means for allowing the manual setting of a low sterilization temperature limit and a high sterilization temperature limit, said temperature range setting means coupled to said controller.

12. The system of claim 10 further comprising time setting means for allowing the manual setting of a sterilization time, said time setting means coupled to said controller.

13. The system of claim 10, wherein said handpiece receptacle includes a cover having a cover latch, said controller being electrically coupled to said cover latch and adapted to command locking or unlocking of said cover latch thereby restricting access to the handpiece during the sterilization process.

14. A sterilization system for a handpiece of a medical or dental device, the sterilization system comprising:

clamp means for holding the handpiece;

current means for supplying current to said clamp means and the handpiece; and control means for adjusting the supply of current by said current means to sterilize the handpiece.

15. The system of claim 14 further comprising temperature range setting means for allowing the manual setting of a low sterilization temperature limit and a high sterilization temperature limit, said temperature range setting means coupled to said control means.

16. The system of claim 14 further comprising time setting means for allowing the manual setting of a sterilization time, said time setting means coupled to said control means.

17. The system of claim 14, wherein said handpiece receptacle includes a cover having a cover latch, said control means electrically coupled to said cover latch and adapted to command locking or unlocking of said cover latch thereby restricting access to the handpiece during the sterilization process.

18. A method of sterilizing a handpiece of a medical or dental device, using a handpiece receptacle with clamps and a current source, the steps comprising:

placing the handpiece in the clamps of the handpiece receptacle;

providing current through the handpiece from the current source;

measuring the temperature of the handpiece;

comparing the temperature of the handpiece with predetermined low and high temperature limits;

adjusting the current provided by the current source to keep the measured temperature between the predetermined low and high temperature limits;

measuring the amount of time the measure temperature has been within the low and high temperature limits; and stopping the current through the handpiece when the measured time has reached a predetermined limit.

19. The method of claim 18 further comprising following said stopping the current step by the steps of:

measuring the temperature of the handpiece;

comparing the temperature of the handpiece with a predetermined handling limit; and allowing the handpiece to be handled when the temperature of the handpiece has dropped below the predetermined handling limit.

20. The method of claim 18, wherein said allowing the handpiece to be handled step includes releasing a lock on a cover of the handpiece receptacle.

* * * * *